United States Patent
Reevell

(10) Patent No.: US 11,083,220 B2
(45) Date of Patent: Aug. 10, 2021

(54) CUSTOMIZABLE DEVICES FOR MULTIPLE CONSUMABLES

(71) Applicant: Altria Client Services LLC, Richmond, VA (US)

(72) Inventor: Tony Reevell, London (GB)

(73) Assignee: Altria Client Services LLC, Richmond, VA (US)

( * ) Notice: Subject to any disclaimer, the term of this patent is extended or adjusted under 35 U.S.C. 154(b) by 308 days.

(21) Appl. No.: 15/987,189

(22) Filed: May 23, 2018

(65) Prior Publication Data

US 2018/0338531 A1 Nov. 29, 2018

Related U.S. Application Data

(63) Continuation of application No. PCT/EP2018/059951, filed on Apr. 18, 2018.

(30) Foreign Application Priority Data

May 23, 2017 (EP) ..................................... 17172521

(51) Int. Cl.
*A24F 47/00* (2020.01)
*A24F 40/30* (2020.01)
(Continued)

(52) U.S. Cl.
CPC .............. *A24F 40/30* (2020.01); *A24F 40/40* (2020.01); *A61M 15/00* (2013.01); *A61M 15/06* (2013.01);
(Continued)

(58) Field of Classification Search
CPC ................................. A24F 40/30; A24F 40/40
See application file for complete search history.

(56) References Cited

U.S. PATENT DOCUMENTS 2,830,593 A * 4/1958 Campbell ............... A24F 13/00
131/361
2012/0048266 A1 3/2012 Alelov
(Continued)

FOREIGN PATENT DOCUMENTS

EP 3219212 A1 9/2017
WO WO-2015/179388 A1 11/2015
(Continued)

OTHER PUBLICATIONS

International Preliminary Report on Patentability for corresponding PCT Application No. PCT/EP2018/059951 dated May 13, 2019.
(Continued)

*Primary Examiner* — Eric Yaary
(74) *Attorney, Agent, or Firm* — Harness, Dickey & Pierce, P.L.C.

(57) ABSTRACT

A customizable device may include a first inhalation device and a second inhalation device, each including a mouth end portion and an upstream end portion. In a storage configuration, the mouth end portion of at least one of the first inhalation device or the second inhalation device is removably coupled to the other inhalation device. In an active configuration, the upstream end portion of at least one of the first inhalation device or the second inhalation device is removably coupled to the other inhalation device. A connector hub may couple the inhalation devices.

17 Claims, 13 Drawing Sheets

(51) Int. Cl.
*A61M 15/00* (2006.01)
*A61M 15/06* (2006.01)
*A24F 40/40* (2020.01)
*A24F 40/10* (2020.01)
*A24F 40/20* (2020.01)
*A24F 40/50* (2020.01)
*H05B 3/00* (2006.01)
*H05B 6/10* (2006.01)

(52) U.S. Cl.
CPC .............. *A24F 40/10* (2020.01); *A24F 40/20* (2020.01); *A24F 40/50* (2020.01); *H05B 3/0014* (2013.01); *H05B 6/10* (2013.01)

(56) References Cited

U.S. PATENT DOCUMENTS

| | | | |
|---|---|---|---|
| 2013/0014772 A1 | 1/2013 | Liu | |
| 2013/0333700 A1 | 12/2013 | Buchberger | |
| 2014/0060556 A1 | 3/2014 | Liu | |
| 2014/0182610 A1* | 7/2014 | Liu | A24F 47/008 131/329 |
| 2014/0366898 A1* | 12/2014 | Monsees | A24F 47/008 131/329 |
| 2015/0196055 A1 | 7/2015 | Liu | |
| 2015/0272221 A1 | 10/2015 | Liu | |
| 2018/0042294 A1* | 2/2018 | Jordil | A24D 3/043 |

FOREIGN PATENT DOCUMENTS

| | | | | |
|---|---|---|---|---|
| WO | WO-2016/075748 A1 | 5/2016 | | |
| WO | WO-2016/124780 A1 | 8/2016 | | |
| WO | WO-2016/135342 A2 | 9/2016 | | |
| WO | WO-2016146780 A1 * | 9/2016 | ............ | A24D 3/043 |

OTHER PUBLICATIONS https://web.archive.org/web/20180416045450/http://jinjiatech.com/PRODUCTS/Heat/91, retrieved on Dec. 7, 2018.
http://www.reuters.com/article/us-brit-am-tobacco-products-idUSKCN0T71U020151118, retrieved on Dec. 4, 2018.
European Search Report for Application No. EP 17172521 dated Nov. 8, 2017.

* cited by examiner

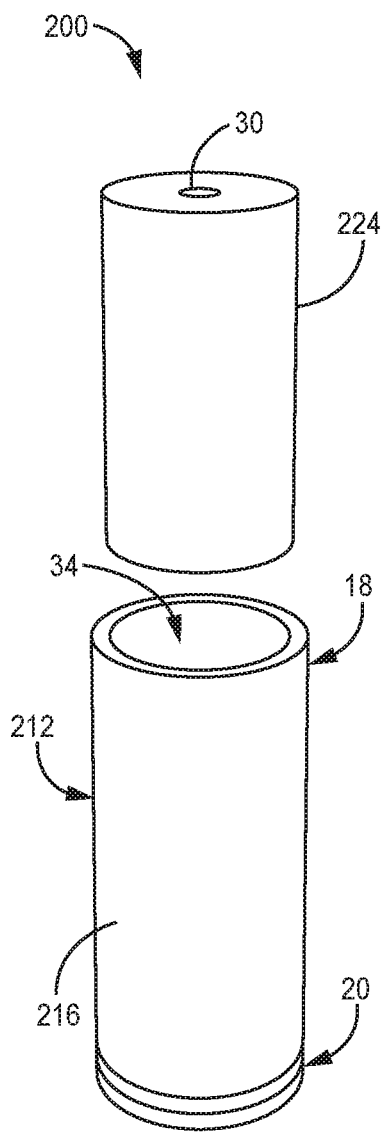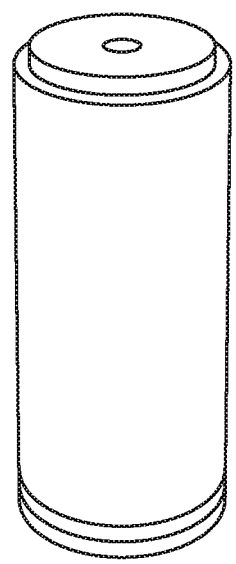
FIG. 8A        FIG. 8B
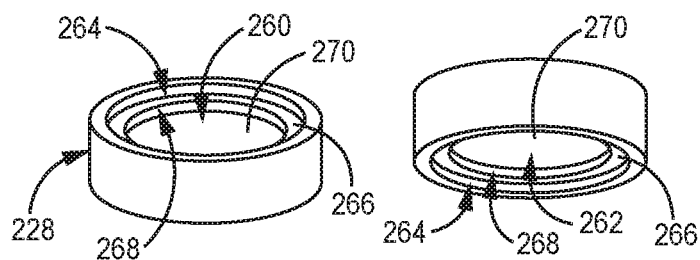
FIG. 8C

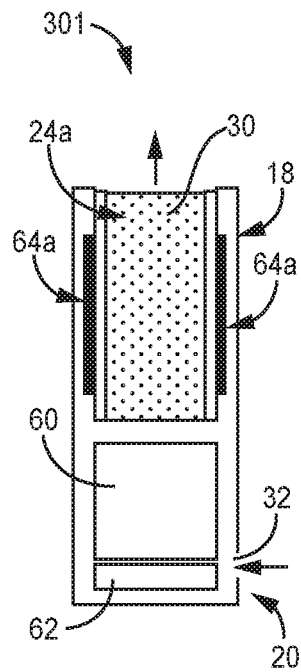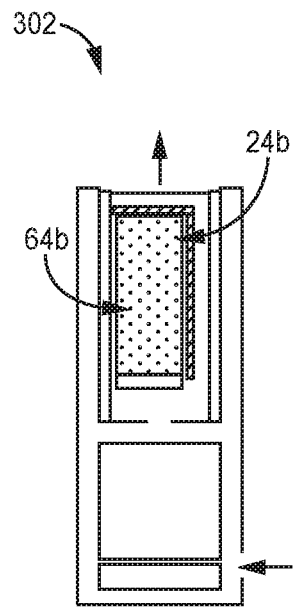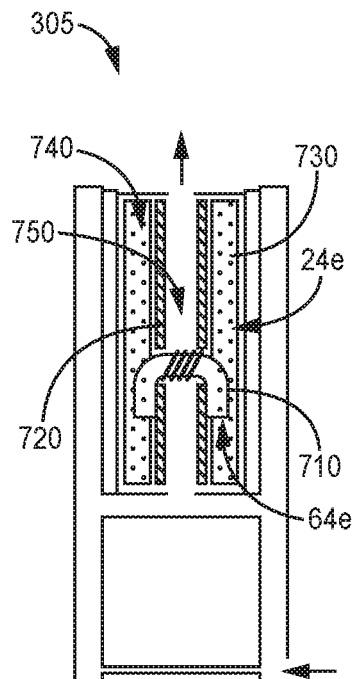
FIG. 12A  FIG. 12B
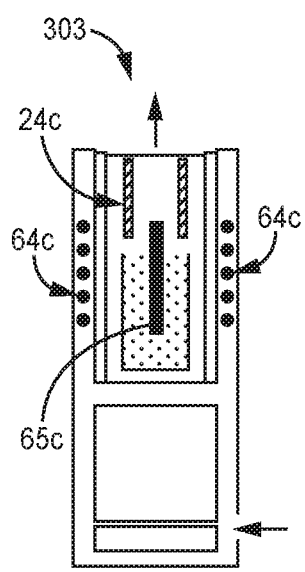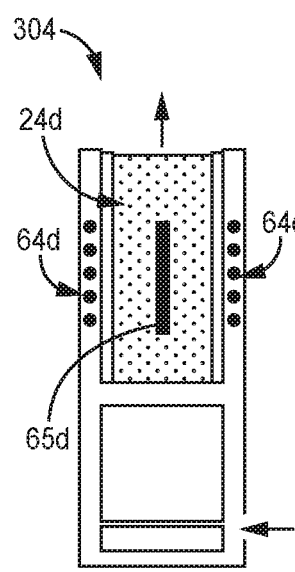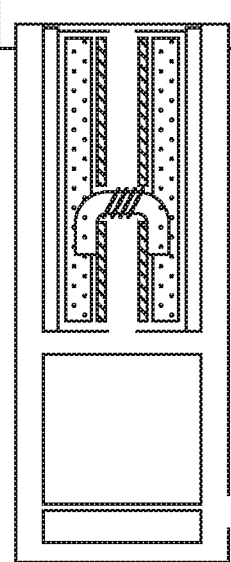
FIG. 12C  FIG. 12D  FIG. 12E

CUSTOMIZABLE DEVICES FOR MULTIPLE CONSUMABLES

CROSS-REFERENCE TO RELATED APPLICATIONS

This is a continuation of and claims priority to PCT/EP2018/059951, filed Apr. 18, 2018, and further claims priority to EP 17172521.1, filed May 23, 2017, both of which are hereby incorporated by reference in their entirety.

BACKGROUND

Field

Example embodiments relate to aerosol-generating devices. The aerosol-generating devices may be suitable for use with more than one consumable and may include different types of consumables.

Description of Related Art

Aerosol-generating devices, such as electronic cigarettes, are known to use a liquid to be evaporated or tobacco material to be heated. In some devices, the evaporation of a liquid is combined with heating tobacco. In other devices, two cartridges with different liquids are provided for selective parallel evaporation of different liquids. When not in use or stored, various devices suffer from leakage of liquid or tobacco through the mouthpieces, which may be particularly problematic when stored in, for example, a pocket of a garment or handbag. Additionally, various devices leave the mouthpiece exposed, even when inactive and not intended to be used. Furthermore, various devices have accessible buttons or switches for activation, which may be susceptible to accidental manipulation and unintended power delivery to a heater.

SUMMARY

A customizable device may include a first inhalation device and a second inhalation device. The first inhalation device includes first end portions including a first mouth end portion and a first upstream end portion. The second inhalation device is removably couplable to either of the first end portions of the first inhalation device. The second inhalation device includes second end portions including a second mouth end portion and a second upstream end portion.

The first inhalation device is configured to be inactive when the first mouth end portion of the first inhalation device is coupled to the second inhalation device.

The first inhalation device is removably couplable to the second upstream end portion of the second inhalation device.

Each of the first end portions of the first inhalation device may define an axially protruding rim removably couplable to either of the second end portions of the second inhalation device.

The customizable device may also include a connector hub. The connector hub may include connector end portions including a first connector end portion and a second connector end portion. The first connector end portion is removably couplable to at least the first end portions of the first inhalation device, and the second connector end portion is removably couplable to at least the second end portions of the second inhalation device.

Each of the connector end portions of the connector hub may be removably couplable to the first end portions of the first inhalation device and the second end portions of the second inhalation device.

An assembly may include a customizable device including a first inhalation device and a second inhalation device. The first inhalation device may include a first housing and a first consumable device within the first housing. The first housing may have first end portions including a first mouth end portion and a first upstream end portion. The first housing may define a first cavity extending between the first mouth end portion and the first upstream end portion. The first consumable device may define a first inhalation port and be disposed in the first cavity such that the first inhalation port is adjacent to the first mouth end portion. The second inhalation device is removably couplable to either of the first end portions of the first inhalation device. The second inhalation device may include a second housing and a second consumable device within the second housing. The second housing may have second end portions including a second mouth end portion and a second upstream end portion. The second housing may define a second cavity extending between the second mouth end portion and the second upstream end portion. The second consumable device may define a second inhalation port and be disposed in the second cavity such that the second inhalation port is adjacent to the second mouth end portion.

At least one of the first consumable device or the second consumable device may include an aerosol-generating substrate containing nicotine.

Each of the first mouth end portion of the first inhalation device and the second mouth end portion of the second inhalation device may define a first engagement feature, and each of the first consumable device and the second consumable device may include a second engagement feature complementary to the first engagement feature to ensure proper alignment.

The first engagement feature may be an axially extending channel, and the second engagement feature may be a radially protruding key.

The first inhalation device may include a first power supply configured to provide energy to heat the first consumable device, and the second inhalation device may include a second power supply configured to provide energy to heat the second consumable device.

The first power supply may include a first controller configured to regulate power delivery from the first power supply, and the second power supply may include a second controller configured to regulate power delivery from the second power supply.

The first controller may be electrically coupled to the second controller to regulate power sharing between the first inhalation device and the second inhalation device.

A method of using a first inhalation device and a second inhalation device may include coupling the first inhalation device and the second inhalation device in series to achieve an active configuration or a storage configuration for each of the first inhalation device and the second inhalation device. The first inhalation device may include first end portions including a first mouth end portion and a first upstream end portion. The second inhalation device is removably couplable to either of the first end portions of the first inhalation device. The second inhalation device may include second end portions including a second mouth end portion and a second upstream end portion.

The coupling may include connecting the first upstream end portion of the first inhalation device to the second mouth end portion of the second inhalation device to achieve the active configuration for the first inhalation device and the storage configuration for the second inhalation device.

The coupling may include connecting the first mouth end portion of the first inhalation device to the second upstream end portion of the second inhalation device to achieve the storage configuration for the first inhalation device and the active configuration for the second inhalation device.

The coupling may include connecting the first upstream end portion of the first inhalation device to the second upstream end portion of the second inhalation device to achieve the active configuration for both the first inhalation device and the second inhalation device.

The coupling may include connecting the first mouth end portion of the first inhalation device to the second mouth end portion of the second inhalation device to achieve the storage configuration for both the first inhalation device and the second inhalation device.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 8A is a perspective view of a first inhalation device with a consumable device to be disposed therein according to an example embodiment.

FIG. 8B is a perspective view of the first inhalation device of FIG. 8A with the consumable device disposed therein.

FIG. 8C are perspective views of a connector hub configured to connect the first inhalation device of FIG. 8B with a second inhalation device.

FIGS. 12A-12E are cross-sectional views of alternative inhalation devices according to an example embodiment.

DETAILED DESCRIPTION

Figure 1:
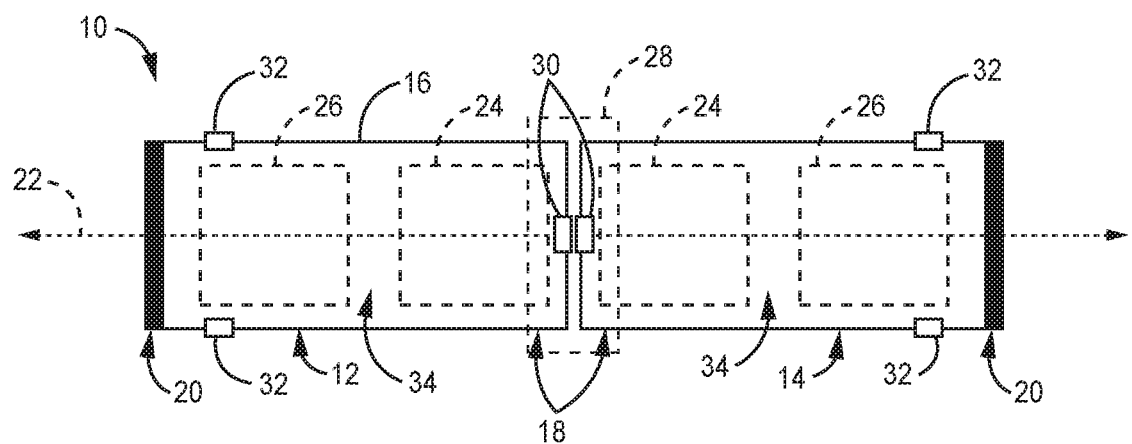
FIG. 1 is a schematic view of a customizable device, wherein the first inhalation device and the second inhalation device are coupled so as to both be in an inactive configuration, according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

The present disclosure provides a customizable aerosol-generating or vaping device including a first inhalation device and a second inhalation device each having a mouth end portion. One or more inhalation devices are removably couplable to the other inhalation device via the mouth end portion. The mouth end portion of the inactive inhalation device may be coupled to the other inhalation device, which may be active. Both inhalation devices may be inactive and coupled to each other by respective mouth end portions in a storage configuration. A connector hub may be coupled between the inhalation devices.

Various aspects of the present disclosure relate to a device including a first inhalation device and a second inhalation device. The first inhalation device has a mouth end portion and an upstream end portion. The second inhalation device has a mouth end portion and an upstream end portion. The first inhalation device is removably couplable to the second inhalation device via the mouth end portion of the first inhalation device. The second inhalation device may be upstream from the first inhalation device.

The first inhalation device may be inactive when the mouth end portion of the first inhalation device is coupled to the second inhalation device. The first inhalation device may comprise a controller configured to inactivate an aerosolizer or enter a power save mode in response to the mouth end portion of the first inhalation device being coupled to the second inhalation device.

The first inhalation device may be active or activatable when the upstream end portion of the first inhalation device is coupled to the second inhalation device. The first inhalation device may be removably couplable to the second inhalation device via the upstream end portion of the second inhalation device.

Each end portion of the first inhalation device may define an axially protruding rim removably couplable to each end portion of the second inhalation device.

The device may further include a connector hub that has a first end portion removably couplable to either end portion of the first inhalation device and a second end portion removably couplable to either end portion of the second inhalation device.

Each end portion of the connector hub may be removably couplable to either end portion of either inhalation device.

Various aspects of the present disclosure relate to an assembly including the device. Each inhalation device includes a housing defining a cavity extending between the mouth end portion and the upstream end portion. Each inhalation device also includes a consumable device disposable in the cavity defining an inhalation port adjacent to the mouth end portion.

At least one consumable device may include an aerosol-generating substrate or pre-vapor formulation having nicotine.

Each mouth end portion of the inhalation devices may define a first feature and each consumable device has a second feature complementary to the first feature to ensure proper relative alignment.

The upstream end portion of one of the inhalation devices may define an axially extending channel engageable with one of the radially protruding keys.

Each inhalation device may include a power supply to provide energy to heat the consumable device.

Each power supply may have a controller to regulate power delivery from the power supply.

The controller may be electrically coupled to the controller of the other inhalation device to regulate power sharing between inhalation devices.

Various aspects of the present disclosure relate to a method of using the device or assembly including coupling the inhalation devices using the mouth end portions to block airflow through the inhalation ports in a storage configuration.

The method may further include coupling the inhalation devices using the mouth end portion of the first inhalation device and the upstream end portion of the second inhalation device to block the first inhalation port and expose the second inhalation port.

Utilizing the customizable aerosol-generating device provides many advantages during use and storage. Different inhalation devices may be attached to one another to provide a variety of choices of different consumable combinations in one customizable device. For example, a choice may be made to make a flavour-based experience and a nicotine-based experience available in one device. Some components of the inhalation devices may be reusable while other components may be disposable or easily replaceable. Electrical connection between the inhalation devices in the storage configuration can also be used for inactivation and robust power management and power savings. The customizable device can be rearranged into a storage configuration that protects and does not expose the mouth end portion. The storage configuration may prevent an inadvertent or unauthorised access to the mouth end. Without access to the mouth end portion, liquid may not be released by inhalation or sucking on the mouth end portion. By sealing the ends of the inhalation device components in the storage configuration, any liquid or other consumable contents that may ordinarily leak may be sealed inside the device until the sections are uncoupled. This can prevent or reduce exposure to consumable contents whilst stored.

The terms "proximal," "upstream," "distal," "downstream," and other terms are used to describe relative positions or orientations of the components of the device. The terms "longitudinal," "axial," "lateral," and "radial," may be used regarding an imaginary longitudinal axis or axial direction, which conceptually may extend through the device. When describing components according to the examples herein, these terms are used irrespective of the orientation of the device being described.

The term "aerosol-generating substrate" or "pre-vapor formulation" refers to a substance, device, or substrate that generates an aerosol or vapor (e.g., substance that releases, upon heating, volatile compounds). Suitable aerosol generating substrates may include plant-based material. For example, the aerosol generating substrate may include tobacco or a tobacco-containing material containing volatile tobacco flavor compounds, which are released from the aerosol generating substrate upon heating. In addition, or alternatively, an aerosol generating substrate may include a non-tobacco containing material. The aerosol generating substrate may include homogenized plant-based material. The aerosol generating substrate may include at least one aerosol former. The aerosol generating substrate may include other additives and ingredients such as flavorants. The aerosol generating substrate may be a liquid at room temperature. For example, the aerosol-forming substrate may be a liquid solution, suspension, dispersion or the like. In some embodiments, the aerosol generating substrate includes glycerol, propylene glycol, water, nicotine and, optionally, one or more flavorants. In a non-limiting embodiment, the aerosol-generating substrate includes nicotine.

The term "consumable" refers to an article including an aerosol-generating substrate or pre-vapor formulation. The contents of the consumable may be used and eventually expended. The consumable may be replaceable for use with the customizable device.

The term "aerosol-generating device" or "consumable device" refers to a device or cartridge including an aerosol generating substrate or other consumable. In some cases, the terms may be used interchangeably. The aerosol-generating device or consumable device may include an aerosolizer, such as an atomizer or heater.

The term "tobacco" refers to a substance including tobacco, which includes tobacco blends or flavored tobacco, for example. Tobacco may be provided in various forms, such as loose tobacco, which does not retain its shape unless disposed in some type of container or reservoir.

The customizable device includes at least a first inhalation device and a second inhalation device. The inhalation devices have a modular form and may be coupled to one another and extend lengthwise along a longitudinal axis. In some embodiments, two inhalation devices are coupled together. The inhalation devices may each form half of the customizable device. In other embodiments, three, four, or more inhalation devices may be coupled together. The inhalation devices may be described as being connected serially or in serial, as opposed to in parallel.

Each inhalation device includes a mouth end portion from which air may be drawn from the inhalation device to use the customizable device. Drawing on one of the inhalation devices causes an aerosol to be entrained in the drawn air from an aerosol-generating substrate of the respective inhalation device. Each inhalation device includes an upstream end portion opposite to the mouth end portion. The upstream end portion may include air inlets to allow air to enter the inhalation device to provide airflow when a draw occurs on the mouth end portion. In some embodiments, when air is drawn from a mouth end portion of one inhalation device of the customizable device, air is not drawn through the other inhalation device. In other words, in some embodiments, only one inhalation device may be used at a time.

Drawing air from the mouth end portion of one of the inhalation devices activates the respective inhalation device, which may be made activatable by the configuration of the inhalation devices. For example, the inhalation device may have a puff sensor configured to activate the device when a puff is detected. An activated inhalation device may generate aerosol from the aerosol-generating substrate, for example, by heating the aerosol-generating substrate. In another instance, the inhalation device may be manually activated.

In some embodiments, the mouth end portion has a different appearance than the upstream end portion. This difference in appearance may help indicate or provide an alert as to the proper end from which to draw air when using the customizable device. The customizable device may not activate when a draw occurs from the upstream end portion. The customizable device may even prevent the drawing of air from the upstream end portion.

The inhalation devices may be removably coupled to one another. One or more inhalation devices may be removably couplable to the other inhalation device via the mouth end portion, upstream end portion, or both. In some embodiments, each end portion of one or more inhalation devices may be coupled to either end portion or another inhalation device. When the upstream end portion is used for coupling, the respective mouth end portion may be exposed for use.

The inhalation devices may be removably connectable to one another so that the devices switch between inactive, active, or activatable states. For example, coupling a first inhalation device to a second inhalation device via the mouth end of the first inhalation device may inactivate the first inhalation device; and coupling the first inhalation device to the second inhalation device via the upstream end portion of the first inhalation device may activate the first inhalation device or place the first inhalation device in an activatable state. Similarly, coupling the second inhalation device to the first inhalation device via the mouth end of the second inhalation device may inactivate the second inhalation device; and coupling the second inhalation device to the first inhalation device via the upstream end portion of the second inhalation device may activate the second inhalation device or place the second inhalation device in an activatable state.

The customizable device may define one or more configurations, each of which may relate to different functionality of the inhalation devices. Configurations of the customizable device may include a storage configuration, a first active configuration, and a second active configuration. In the storage configuration, the inhalation devices may each be coupled to one another via the mouth end portions, which may inactivate both devices. The upstream end portions may be closed or sealed. The customizable device may be considered closed or sealed for storage when in the storage configuration. In the first active configuration, the upstream end portion of the first inhalation device may be coupled to the mouth end portion of the second inhalation device. The first active configuration may activate, or make activatable, the first inhalation device and inactivate the second inhalation device. In the second active configuration, the upstream end portion of the second inhalation device may be coupled to the mouth end portion of the first inhalation device. The second active configuration may activate, or make activatable, the second inhalation device and inactivate the first inhalation device.

An optional third configuration may activate, or make activatable, both the first and second inhalation devices when both are coupled via the upstream end portions. Alternatively, the third configuration may inactivate both devices.

The inhalation devices may be coupled to one another using any suitable techniques, which may include a hub disposed between the inhalation devices. Non-limiting examples of suitable coupling techniques include friction fit, screw fit (e.g., threading), bayonet fit, magnetic fit, or other suitable techniques to axially retain the inhalation devices adjacent to, in proximity to, or in contact with one another. In some embodiments, the inhalation devices are secured together using friction fit engagement. In some embodiments, the hub and the inhalation devices are secured together using a screw fit or friction fit engagement.

One or more inhalation devices may be described as an assembly including at least one consumable device. In some embodiments, each inhalation device includes one consumable device. In other embodiments, each inhalation device includes two or more consumable devices. The consumable device may have an aerosol-generating substrate. The aerosol-generating substrate may have nicotine.

Substances from an aerosol-generating substrate contained in the consumable device may be transported by an airflow passing through the substrate or through the consumable device, respectively. These substances may be entrained by the passing airflow. For example, an airflow passing a tobacco substrate may be entrained with tobacco flavour. The substances to be inhaled may also actively be generated, for example, by heating a substrate contained in the consumable device and forming an inhalable aerosol. Also, other atomization processes may be used for aerosol generation.

The first inhalation device may include a first consumable device. The second inhalation device may include a second consumable device. In some embodiments, the consumable devices are different types, such as a liquid-containing consumable and solid substrate-containing consumable. In other embodiments, the consumable devices are the same type. Even if the consumable devices are of the same types, the consumable devices may contain a different consumable composition, for example, having different flavour or different substance combination. The device may be varied and customized by selecting appropriate consumables for the inhalation devices to form a single, customizable device.

In some embodiments, different consumable devices contain any one or a combination of different aerosol-forming substrates, for example different tobacco materials, different flavours, different nicotine contents, and/or other different substance combinations. In some embodiments, consumables may differ in the manner of aerosolizing the substrate.

In some embodiments, different consumables may have both a different aerosol-forming substrate and manner of aerosolizing the substrate.

One or more types of consumable devices may be used or may be determined to be usable with the inhalation devices. Examples of consumable device types are, for example, but not limited to: liquid-containing cartridges or tank systems including or excluding an integrated aerosolizing element such as, for example, cartomizers (combined cartridge and atomizer); solid substrate-containing consumables such as, for example, tobacco-containing plugs; solid substrate-containing capsules, wherein the solid substrate may be tobacco material, homogenized tobacco material or substrate in powder form; vaporisable wax; tobacco sheets that are gathered or crimped. Some consumable devices may be described as e-cigarette (e.g., e-cig) vaporisers, heated tobacco, or vaporisable wax.

The consumable devices may make use of different techniques for aerosolizing, or releasing inhalable substances from, the consumables. For example, when one consumable device has a heatable liquid, another consumable device may be a tobacco substrate or may contain a non-heated but otherwise atomized substrate. Some consumables require different temperatures to generate aerosol from the aerosol-generating substrate.

In some embodiments, one or more consumable devices includes at least part of a heater for properly heating the one or more specific consumables. In some embodiments, one or more consumable devices do not include any part of a heater. The heater may be part of the inhalation device but entirely external to the consumable.

In some embodiments, one or more consumable devices include a tobacco consumable. The inhalation device may include heaters external to the consumable device to heat the tobacco.

In various embodiments, one or more consumable devices include a heated mesh e-cig consumable. The inhalation device may deliver power to the consumable, particularly the heater mesh, to heat the substrate.

In some further embodiments, one or more consumable devices include an e-cig consumable with a susceptor. The inhalation device may include an induction coil external to the consumable device to heat the substrate.

In still further embodiments, one or more consumable devices include a heated tobacco consumable with a susceptor. The inhalation device may include an induction coil external to the consumable device to heat the substrate.

In yet further embodiments, one or more consumable devices include a conventional heated-coil e-cig consumable. The inhalation device may deliver power to the consumable, particularly the heated-coil, to heat the substrate.

In some embodiments, the inhalation devices have the same or similar outward appearance while having distinct functions. For example, the first inhalation device may include an induction heater, and the second inhalation device may include an e-cig connection or conventional tobacco heater.

One or more inhalation devices may include a housing to receive at least one of the consumable devices. The housing may at least partially define an outermost surface of the inhalation device. The housing may define one or more cavities to receive one or more consumable devices between the mouth end portion and the upstream end portion. The cavity may extend from an opening at the mouth end portion, for example, to receive one of the consumable devices. In some embodiments, each inhalation device includes a housing that defines one cavity to receive one consumable device. In other embodiments, the housing defines two or more cavities to receive two or more consumable devices.

The housing may be a rigid housing. Any suitable material or combination of materials may be used for forming the rigid housing. Examples of suitable materials include metals, alloys, plastics or composite materials containing one or more of those materials, or thermoplastics that are suitable for food or pharmaceutical applications, for example polypropylene, polyetheretherketone (PEEK), acrylonitrile butadiene styrene and polyethylene.

The housing may define one or more air inlets, for example, adjacent to, in proximity to, or at the upstream end portion. One or more passages within the housing, which may be at least partially through the consumable device, may fluidly couple the air inlets to the inhalation port of the consumable device. In some embodiments, the air inlets may include radial air inlets, which may extend through a side wall of the housing. In some embodiments, the air inlets may include axial air inlets, which may extend through an end wall of the housing.

The consumable device may take any suitable shape for engaging with the inhalation device and produce aerosol. In some embodiments, one or more of the inhalation devices may be able to accept multiple types of consumable devices. In some embodiments, one or more of inhalation devices may be able to accept only a single type of consumable device. The customizable device may include a multiple-type inhalation device, single-type inhalation devices, or combinations thereof. In some embodiments, the consumable devices may have a conventional and familiar cylindrical shape. The inhalation device may accept conventionally-shaped consumable devices to provide ease of manufacturing.

One or more consumable devices may have the same shape and size. In some embodiments, all consumable devices have a universally similar shape in one or more dimensions, for example, the same outer or inner diameter or the same overall or cavity length. In other embodiments, different consumable devices may differ in shape in one or more dimensions.

Each consumable device may have an inhalation port. The consumable device may be inserted into the cavity such that the inhalation port is adjacent to, or in proximity to, the mouth end portion of the inhalation device. When the mouth end portion is used to couple the inhalation device, the inhalation port may also be unexposed, or considered blocked for purposes of inhalation. Likewise, when the mouth end portion is free from coupling, the inhalation port may be exposed, or considered available for purposes of inhalation.

Each consumable device may have an internal port. The internal port may be disposed within the housing to receive airflow from the air inlet of the housing. The internal port may be in fluid communication with the inhalation port to allow airflow from the inlet port to the inhalation port when the consumable is disposed within the cavity. In some embodiments, airflow may also activate a sensor of the consumable device, which may activate aerosolizing of the consumable or indicate an amount of consumable remaining.

In the storage configuration, the inhalation port of the first consumable device of the first inhalation device may be adjacent to, in proximity to, or in contact with the inhalation port of the second consumable device of the second inhalation device. The housing of the inhalation devices may close or seal the consumable devices from exposure, which may provide a convenient format for transporting and storing the customizable device. In this storage configuration, the customizable device may also prevent the use of either consumable device.

In the first active configuration, the inhalation port of the first consumable device of the first inhalation device may be exposed, whereas the inhalation port of the second consumable device of the second inhalation device may be unexposed or used for coupling to the first inhalation device. The second consumable device may be closed or sealed from exposure to prevent the use of the second consumable device while allowing use of the first consumable device.

The second active configuration may be considered the opposite of the first active configuration. In the second active configuration, the inhalation port of the second consumable device of the second inhalation device may be exposed, whereas the inhalation port of the first consumable device of the first inhalation device may be unexposed or used for coupling to the second inhalation device. The first consumable device may be closed or sealed from exposure to prevent the use of the second consumable device while allowing use of the first consumable device.

Each consumable device may partially or entirely be inserted into a cavity. The end of the consumable device having the inhalation port may be sub flush, flush, or super flush (e.g., partial insertion) with the mouth end portion of the housing of the inhalation device. Partial insertion may facilitate the removal of the consumable after being expended. For example, an end portion of the consumable device may be gripped for removal from the cavity.

One or more consumable devices may be a single or modular integrated unit. In some embodiments, the consumable device may include an aerosol-generating substrate contained in a capsule, cartridge, reservoir, matrix, or other suitable container and a vaporizing unit that can engage with the capsule. When connected, the vaporizing unit may be powered to aerosolize an aerosol-generating substrate. The container may be considered disposable, whereas the vaporizing unit may be considered reusable over the lifetime of multiple capsules.

One or more consumable device may include protrusions to facilitate the insertion and removal of the consumable device from the cavity. In some embodiments, the consumable device includes a radially protruding key. The key may extend outwardly from an outer surface of the consumable device. The key may be disposed adjacent to, in proximity to, or at the end of the consumable device with the inhalation port. The key may be any suitable shape that facilitates engagement, such as a rectangular prism.

The housing of one or more inhalation devices may include axially extending channels, or cut outs, to accommodate one or more keys of a consumable device. Each channel may extend through the housing (e.g., from the cavity to an exterior of the housing). In some embodiments, each housing defines a channel extending from the mouth end portion toward the upstream end portion. In some embodiments, one or more housings define a channel extending from the upstream end portion toward the upstream end portion. In some embodiments, each housing may include at least one channel. In some embodiments, one of the inhalation devices may include at least one channel in each end portion.

The length of the channel may be sufficient to receive at least one, two, or more keys. The one or more keys may be slidable into an open end of the channel. The cooperation of at least one key and one of the channels may limit the axial movement of the consumable device relative to the housing in at least one direction and may limit the rotational movement of the consumable device relative to the housing in at least one direction. Limited rotational movement may facilitate alignment of electrical contacts described herein. Alternatively, the consumable device may include an indent or channel and the housing includes a detent or protrusion to provide the same or similar functionality.

The housing of one or more inhalation devices may define an axially protruding rim. The channel may be formed in the axial protruding rim. The rim may be used to couple to the axially protruding rim of the housing of another inhalation device.

In some embodiments, the housings of the inhalation devices may be similar, for example, in diameter, but have different end portions. For example, a first inhalation device may include an axially protruding rim at each end portion defining a same inner diameter, and the second inhalation device may have an axially protruding rim at each end portion defining a same outer diameter. The inner diameter and the outer diameter may be sized to cooperatively engage one another to couple the inhalation devices together. Either end of the first inhalation device may couple to either end the second inhalation device due to the cooperating sizes of the respective inner and outer diameters. In some embodiments, the consumable devices used may have an identical outermost shape.

In various embodiments, the axially protruding rims of the first inhalation device may each have an axially extending channel. A first channel adjacent to the mouth end portion may have a first length greater than a second length of the second channel adjacent to the upstream end portion. For example, the first channel may accommodate two consumable keys, and the second channel may accommodate only one consumable key (e.g., half the length). When disposed into the cavity of the first inhalation device, the first consumable may be sub flush with the mouth end portion of the housing. The first consumable device may have a radially protruding key that slidably engages the first channel.

The second inhalation device may have only one axially extending channel adjacent to the mouth end portion. When disposed into the cavity of the second inhalation device, the second consumable may be flush with the mouth end portion of the housing. The second consumable device may have a radially protruding key that slidably engages the channel of the second inhalation device.

In the storage configuration, the mouth end portion of the second inhalation device may be at least partially inserted into the mouth end portion of the first inhalation device in embodiments where the first consumable is sub flush with the mouth end portion of the first inhalation device. The radially protruding key of the second consumable may engage the first channel adjacent to the mouth end portion of the first inhalation device. In the first active configuration, the mouth portion of the second inhalation device may be at least partially inserted into the upstream end portion of the first inhalation device. The radially protruding key of the second consumable may engage the second channel adjacent to the upstream end portion of the first inhalation device. In the second active configuration, the upstream end portion of the second inhalation device may be at least partially inserted into the mouth end portion of the first inhalation device. In the third configuration, the upstream end portion of the second inhalation device may be at least partially inserted into the mouth end portion of the first inhalation device.

The customizable device may include a connector hub removably coupled between the inhalation devices in various configurations. The hub may be a separate component, independently couplable to one or more ends of the inhalation devices. Each end portion of each inhalation device may have the same one or more dimensions to facilitate coupling of any end of the inhalation devices to the hub. One or more of the dimensions of the outermost surface of the inhalation device housing may be the same or identical.

In some embodiments, air inlets of an inhalation device are not blocked, closed, or sealed by the hub when connected to the upstream end portion to allow for use of the inhalation device. The inhalation port of the consumable, the opening of the housing at the mouth end portion, or both may be blocked, closed, or sealed by the hub when connected to the mouth end portion.

The hub may include a first end portion and a second end portion. The second end portion may be disposed opposite to the first end portion. A recess may be defined in each end portion to at least partially receive one end of one of the inhalation devices. Each end portion of the hub may be the same or similar. In some embodiments, each recess of the hub is the same or similar. In some embodiments, the first end portion may be removably coupled to either end portion of the first inhalation device and a second end portion removably coupled to either end portion of the second inhalation device.

Each recess may define a first inner diameter. The first inner diameter may be sized to cooperatively engage an outer diameter of the housings of the inhalation devices to couple the hub to the inhalation device.

Each recess may define a second inner diameter less than the first inner diameter. In some embodiments, the second inner diameter is defined by a shoulder formed in the recess sub flush the respective end portion. The first inner diameter may be defined above the shoulder and the second inner diameter may be defined by the shoulder. In some embodiments, the second inner diameter may be sized to cooperatively engage an outer diameter of a consumable device to couple the hub to the consumable device. For example, the consumable device may be partially disposed within the cavity of the inhalation device and be super flush with the mouth end portion. The hub may engage both the housing at the first inner diameter and the consumable device at the second inner diameter.

One or more inhalation devices may include an aerosolizer (e.g., atomizer or heater). The aerosolizer may be disposed within (e.g., internal to the outermost surface of) the inhalation device housing. In some embodiments, one or more inhalation devices includes a heater. In some embodiments, aerosolization of the aerosol-generating substrate of the consumable may be accomplished by heating. The substrate may be heated via a heating element in the consumable device or by providing a heating element in the housing external to the consumable device. When a heating element or atomization element is disposed in the consumable device itself, the cavity may include corresponding electrical contacts for providing electrical power from a power supply, which may be at least partially disposed in the housing, to the aerosolizer in the consumable device.

Heating of the consumable may be performed resistively or inductively. A resistively heatable heating element may be provided in the consumable device (e.g., mesh) or in the housing external to the consumable device (e.g., resistive conductors). With inductive heating, an inductor, for example an induction coil, may be provided in a housing external to the consumable device. A susceptor material heated by the inductor may be provided in the housing external to the consumable device, in the housing and configured to pierce into the consumable, or in the consumable device itself.

In some embodiments, one or more inhalation devices include a heating element, electrical contacts, or both. Including both may provide many options for different consumable devices to be used with the inhalation device. It may not be required to check whether a particular inhalation device is adapted for a specific consumable that does or does not have, for example, a heater.

A heating element in the device may be arranged in or adjacent to a wall of the housing adjacent to the consumable device in the cavity. In some embodiments, resistively heatable metal tracks or resistively heatable wires may be disposed in or adjacent to the wall of the housing or resistively heatable wires may be arranged in the receiving chamber wall to heat the substrate. In some embodiments, an inductor in the form of an induction coil may be arranged in or adjacent to a wall of the housing adjacent to the consumable device, which may surround the consumable device. A susceptor may be disposed within the consumable device operatively coupled to the induction coil to receive electromagnetic power to heat the substrate.

A heating element in the inhalation device may extend into the cavity. For example, the heating element may be a resistively heated heater blade or an elongated susceptor.

One or more inhalation devices may include a power supply. The power supply may include a power source and a controller. The power source may be, for example, a battery or a capacitor. The power supply may be at least partially disposed in the housing external to the consumable device. The power supply may provide energy to heat the aerosol-generating substrate in the consumable device.

The controller may be considered part of the power supply or separate. The controller may be at least partially disposed in the housing external to the consumable device. The controller may to regulate power delivery from the power supply to one or more consumable devices (e.g., power management. In some embodiments, the controller may be configured to regulate delivery of an aerosol resulting from heating of the substrate.

In some embodiments, the controller is electrically coupled to the controller of the other inhalation device to regulate power sharing between inhalation devices or, for example, to communicate between inhalation devices. In some embodiments, the hub may include a controller to facilitate power sharing between inhalation devices or, for example, to facilitate communication between the controllers of the inhalation devices.

The controller can be provided in any suitable form and may, for example, include a processor, a memory, or both. The controller can include one or more of an Application Specific Integrated Circuit (ASIC) state machine, a digital signal processor, a gate array, a microprocessor, or equivalent discrete or integrated logic circuitry. The controller can include memory that contains instructions that cause one or more components of the inhalation device to carry out a function or aspect of the inhalation device. Functions attributable to the controller in this disclosure can be embodied as one or more of software, firmware, and hardware.

The inhalation devices may include electrical or electronic circuitry to operatively connect the controller to the power supply and the consumable device. In some embodiments, the circuitry includes electrical contacts exposed at one or more end portions of the inhalation device. The electrical contacts may be disposed in or on the housing. In some embodiments, the electrical contacts are exposed axially in the rim of the inhalation device. The electrical contacts may be used for power sharing or data sharing between inhalation devices. In some embodiments, the hub may include electrical contacts, as well as electrical or electronic circuitry, to facilitate power sharing between inhalation devices or, for example, to facilitate communication between the controllers of the inhalation devices.

Power sharing may include providing power from the power supply in one inhalation device, which may be inactive, to the consumable device in the other inhalation device, which may be active. This type of power sharing may be used, for example, when the power supply of the active device has been expended. Power sharing may also include charging the power supply of an inactive inhalation device (e.g., with a lower charge) with the power supply of the other inactive inhalation device (e.g., with a higher charge), for example, in the storage configuration. This type of power sharing may balance the charges in each power supply. Power sharing may facilitate extended operation of one or more inhalation devices before recharging or replacing the battery. In other embodiments, the inhalation devices may not share power in the storage configuration.

The controller may also facilitate power management in response to the configuration of the customizable device. In some embodiments, the inhalation devices may enter a power saving mode in response to the storage configuration. In some embodiments, the first active configuration may turn on the first inhalation device and turn off the second inhalation device, or vice versa for the second active configuration. In some embodiments, the controller may inactivate the inhalation device until the inhalation device is coupled to another inhalation device or hub. In other embodiments, controller allows activation of the inhalation device whether or not the inhalation device is coupled to another inhalation device or hub.

One or more inhalation devices may include an activator. The activator may be part of the controller. The activator may provide a signal or modify a connection to indicate that the heater should be turned on. The activator detects an action indicating an intent to use the customizable device. The action may be, for example, a puff or manual engagement.

In some embodiments, the activator includes a puff sensor. The activator may detect when a puff occurs (e.g., drawing of air) on the customizable device and, in response, the controller may turn on the heater to begin generating aerosol from the substrate. Non-limiting types of puff sensors may include one or more of a vibrating membrane, a piezoelectric sensor, a mesh-like membrane, a pressure sensor (e.g., capacitive pressure sensor), and an airflow switch.

In some embodiments, the activator includes a user-engageable interface. The activator may detect engagement by a user and, in response, the controller may turn on the heater. Non-limiting types of user-engageable interfaces may include one or more of a button or a switch.

The controller may turn off the heater, for example, in response to the end of a puff, after a predetermined amount of time in response to the end of the puff, or in response to detecting that a consumable has been expended.

The controller may actively prevent the heater from being turned on when the inhalation device is in the inactive position. For example, in the storage configuration, both inhalation devices may be considered inactive. In some embodiments, the controller may allow the inhalation device to be used independently when uncoupled from another inhalation device or hub. In some embodiments, the controller may prevent the heater from being turned on unless the inhalation device is coupled to another inhalation device or hub and in the active position.

One or more components of the customizable device may be considered reusable. Non-limiting examples of reusable components include one or more of: the housing, the hub, the power supply, the heater, and the activator. One or more components of the customizable device may be considered disposable. Non-limiting examples of disposable components include one or more of: the consumable device, the consumable, the aerosol-generating substrate, the heater, the activator, and the power supply. The housing, the hub, the power supply, the heater or some components thereof, and the activator may be reusable over the lifetime of multiple consumable devices.

The customizable device may be used in any suitable manner to provide inhalable aerosol and to store the device. Before use, the inhalation devices may be coupled using the mouth end portion of the first inhalation device and the upstream end portion of the second inhalation device to block the first inhalation port and expose the second inhalation port, or vice versa. The second inhalation device may be used in this configuration, or vice versa. To store the device, the inhalation devices may be coupled using the mouth end portions to block airflow through the inhalation ports in a storage configuration. The customizable device may be used simply to activate and inactivate inhalation devices as desired.

Figure 2:
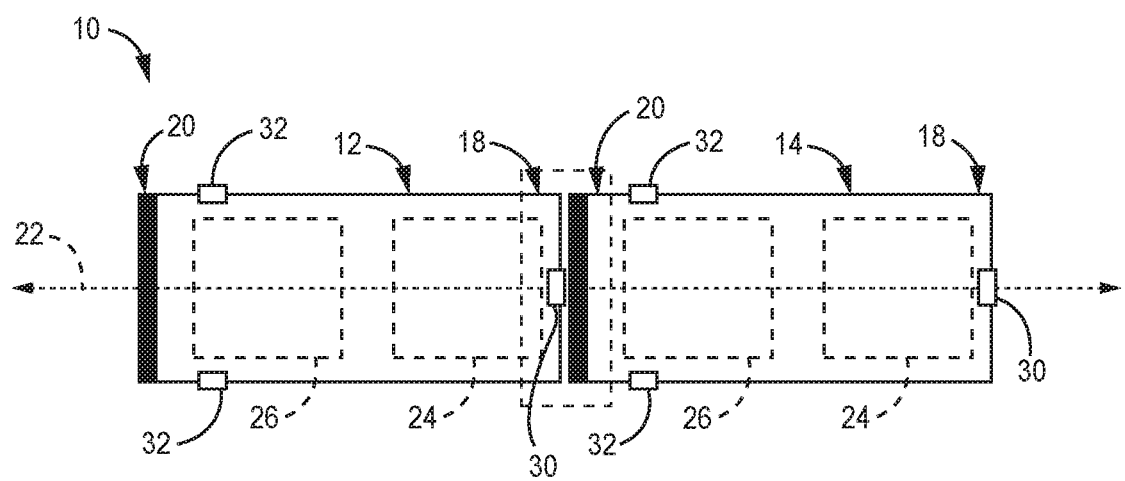
FIG. 2 is a schematic view of the customizable device of FIG. 1, wherein the first inhalation device and the second inhalation device are coupled so as to be in an inactive configuration and an active configuration, respectively.

FIGS. 1-2 are schematic diagrams of an illustrative customizable device 10. FIG. 1 shows the customizable device 10 in a storage or closed configuration. FIG. 2 shows the customizable device 10 in a configuration in which a second inhalation device 14 is in an active configuration and a first inhalation device is in an inactive configuration. Customizable device 10 includes a first inhalation device 12 removably coupled to a second inhalation device 14. Each inhalation device 12, 14 includes a housing 16 extending longitudinally along a longitudinal axis 22 from a mouth end portion 18 and an upstream end portion 20. In the closed configuration of FIG. 1, the respective mouth end portions 18 are coupled to one another. Both inhalation devices 12, 14 are inactive in the closed configuration. In the illustrated active configuration of FIG. 2, the mouth end portion 18 of the first inhalation device 12 is coupled to the upstream end portion 20 of the second inhalation device 14. The second inhalation device 14 is active in such an example embodiment, whereas the first inhalation device 12 is inactive.

Each inhalation device 12, 14 includes a consumable device 24 and a power supply 26. The consumable device 24 may be removable from the housing 16. Each consumable device 24 may have an aerosol-generating substrate, which may include nicotine. The customizable device 10 may include an optional connector hub 28 that facilitates coupling ends of the inhalation devices 12, 14. Each inhalation device 12, 14 may be about equal in length along the longitudinal axis 22.

The inhalation devices 12, 14 each include one or more inhalation ports 30. The inhalation ports 30 may be defined by the consumable devices 24. Air may be drawn through the inhalation ports 30. In response, air may be drawn into the cavity 34 of the respective inhalation device 12, 14 through one or more air inlets 32, which may be defined in the housing 16 of the respective inhalation device. The inhalation ports 30 are axial ports, which extend axially parallel to the longitudinal axis 22 and may be disposed on an axial-facing surface. The air inlets 32 are radial air inlets, which may extend radially relative to the longitudinal axis 22 and may be disposed on a radial-facing surface.

FIGS. 3A-7B show various views of an illustrative customizable device 100 having first inhalation device 112 having axially protruding rims 40, 41 removably coupled to a second inhalation device 114. Many of the parts and components depicted in FIGS. 3A-7B are the same or similar to those depicted in, and described with regard to, FIGS. 1-2. Reference is made to the discussion above for numbered elements depicted in, but not specifically discussed herein.

The first inhalation device 112 includes axially protruding rim 40 extending from the mouth end portion 18 and axially protruding rim 41 extending from the upstream end portion 20. The second inhalation device 114 includes an axially protruding rim 42 extending from the mouth end portion 18 and an axially protruding rim 43 extending from the upstream end portion 20. The axially protruding rims 40, 41 of the first inhalation device 112 define a same inner diameter. The rims 42, 43 of the second inhalation device 114 define a same outer diameter that is complementary to the inner diameter of the rims 40, 41 to removably couple the inhalation devices 112, 114.

Axially protruding rim 40 defines one or more axially extending channels 44 adjacent to, in proximity with, or at the mouth end portion 18. Rim 41 defines one or more axially extending channels 45 adjacent to, in proximity with, or at the upstream end portion 20. Rim 42 defines one or more axially extending channels 46 adjacent to, in proximity with, or at mouth end portion 18. Rim 43 does not define an axially extending channel.

Figures 3A, 3B:
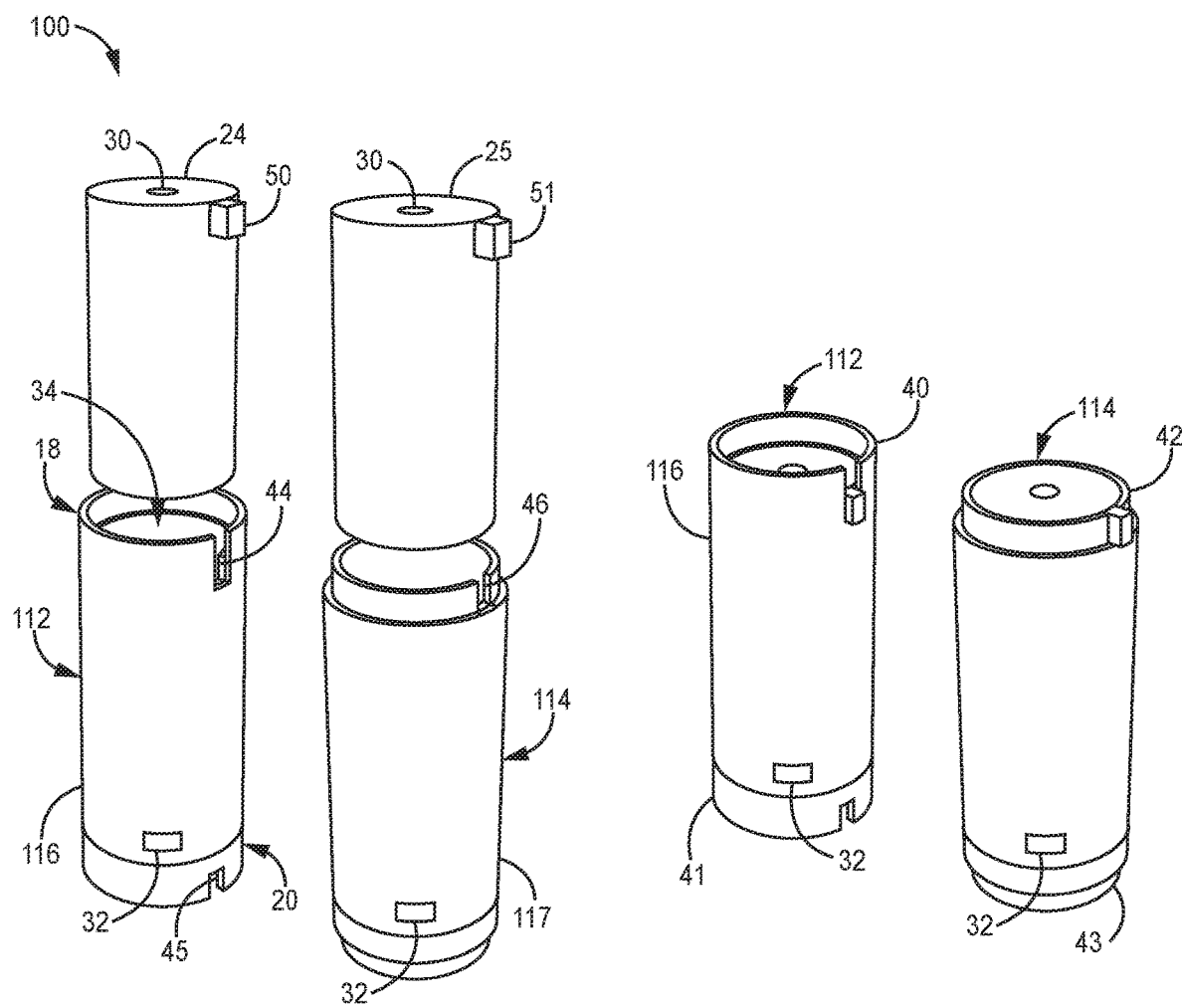
FIG. 3A is a perspective view of a customizable device including a first inhalation device with a first consumable device to be disposed therein and a second inhalation device with a second consumable device to be disposed therein according to an example embodiment.
FIG. 3B is a perspective view of the customizable device of FIG. 3A, wherein the first consumable device is disposed in the first inhalation device and the second consumable device is disposed in the second inhalation device.

A first and second consumable device 24, 25 each are disposable within the housing 116, 117 of one of the inhalation devices 112, 114 (see FIG. 3B). The consumable devices 24, 25 and the housings 116, 117 may have a generally cylindrical shape. The consumable devices 24, 25 may be the same shape. The first consumable device 24 may be disposed sub flush with the mouth end portion 18 of the first inhalation device 112. The second consumable device 25 may be disposed flush with the mouth end portion 18 of the second inhalation device 114.

The first consumable device 24 includes a radially protruding key 50 and may be inserted into the housing 116 of the first inhalation device 112. The key 50 slidably engages into the channel 44. The second consumable device 25 includes a radially protruding key 51 and, as shown in FIG. 3B, is insertable into the housing 117 of the second inhalation device 114. The key 51 slidably engages into the channel 46. The keys 50, 51 may facilitate alignment of the inhalation devices 112, 114 when coupled and may facilitate removing the consumable devices 24, 25 from the respective housing 116, 117.

Figure 4A:
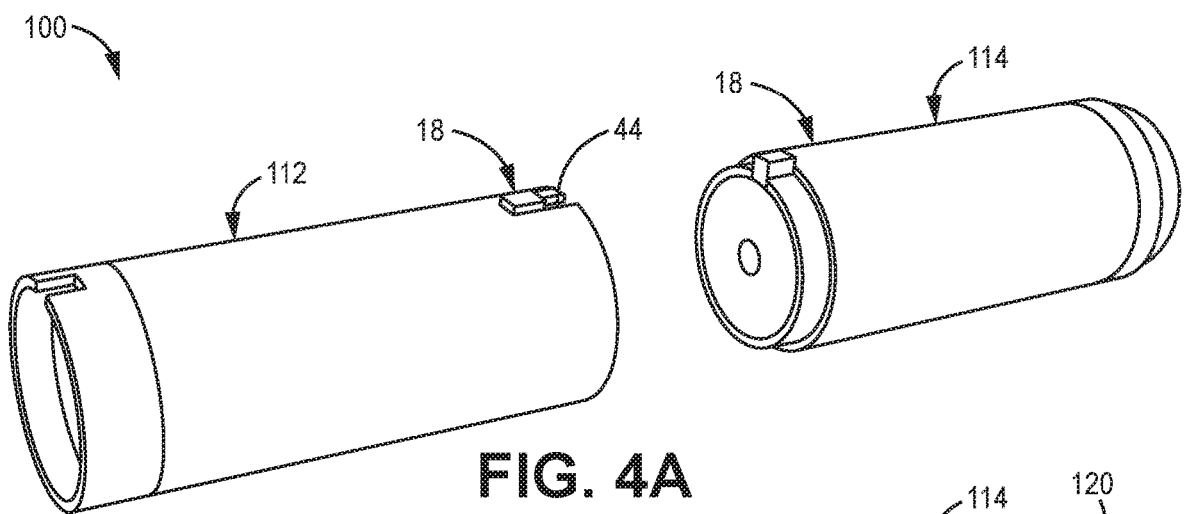
FIGS. 4A-4B are perspective views of the customizable device of FIG. 3B, wherein the first inhalation device and the second inhalation device are coupled so as to both be in an inactive configuration.
Figure 4B:
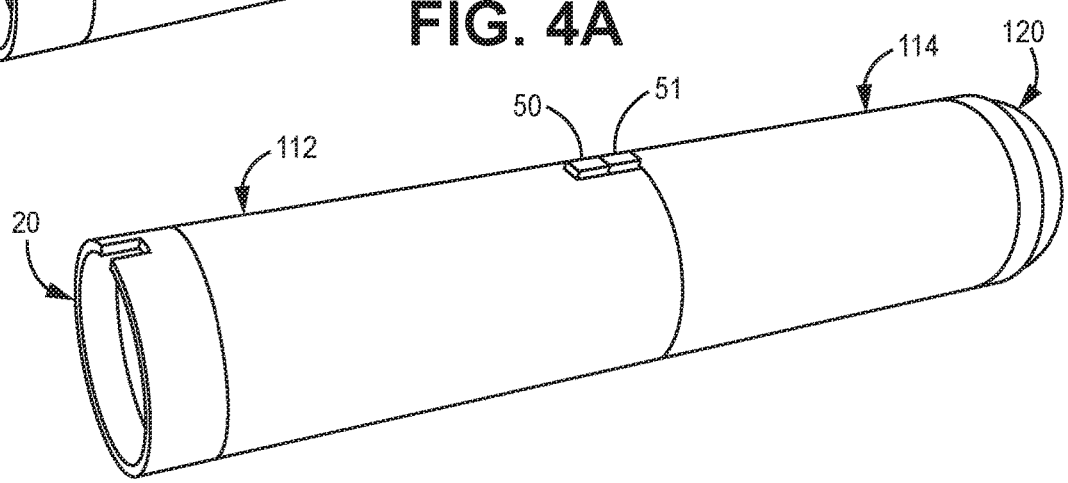

In the storage configuration shown in FIGS. 4A-B, the mouth end portions 18 of the inhalation devices 112, 114 are removably coupled. Both devices 112, 114 are inactive in the storage configuration. The keys 50, 51 are aligned serially and inserted into the channel 44. The channel 44 may extend twice the distance into the respective housing 116, 117 as the other channels 45, 46.

Figure 5A:
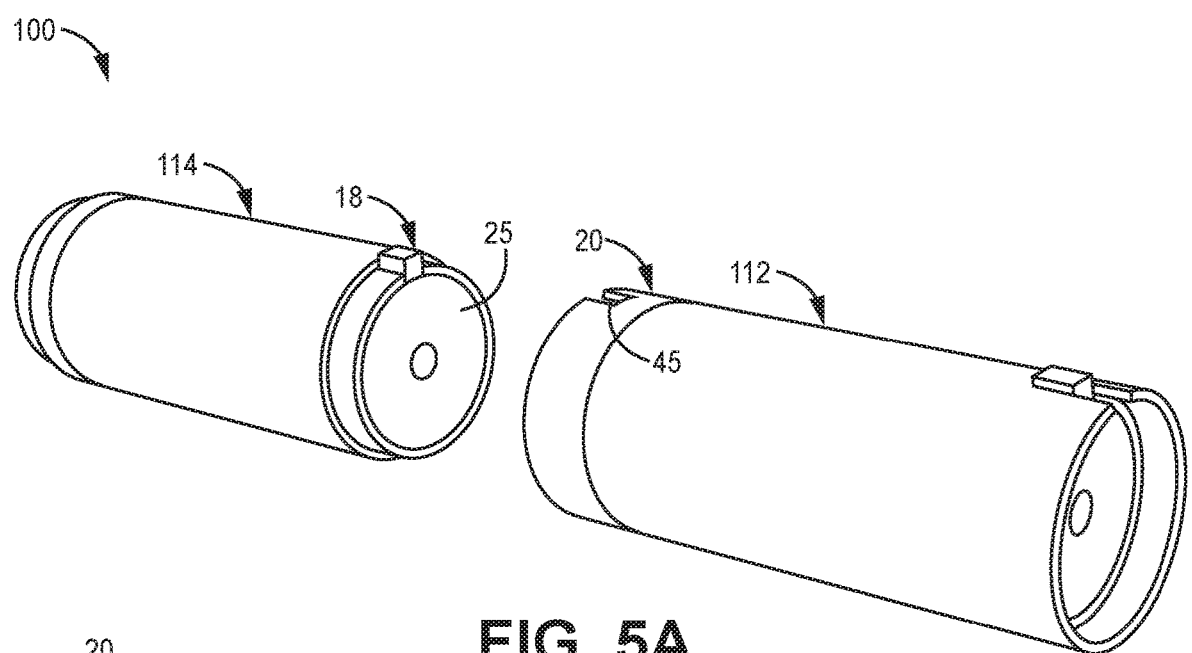
FIGS. 5A-5B are perspective views of the customizable device of FIG. 3B, wherein the first inhalation device and the second inhalation device are coupled so as to be in an active configuration and an inactive configuration, respectively.
Figure 5B:
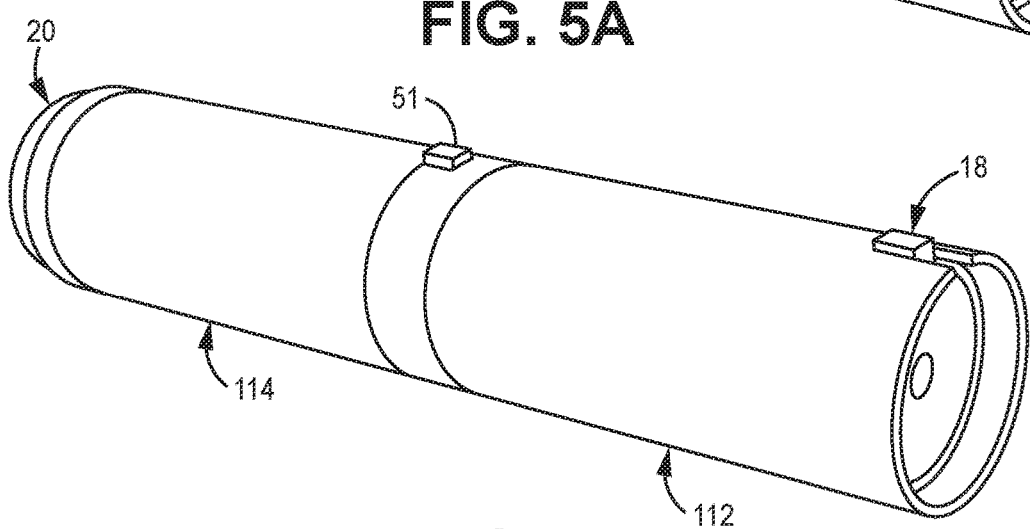

In the first active configuration shown in FIGS. 5A-B, the mouth end portion 18 of the second inhalation device 114 is removably coupled to the upstream end portion 20 of the first inhalation device 112. In this configuration, the first inhalation device 112 is active, whereas the second inhalation device 114 is inactive. The key 51 of the second consumable device 25 is inserted into the channel 45 of the first inhalation device 112.

Figure 6A:
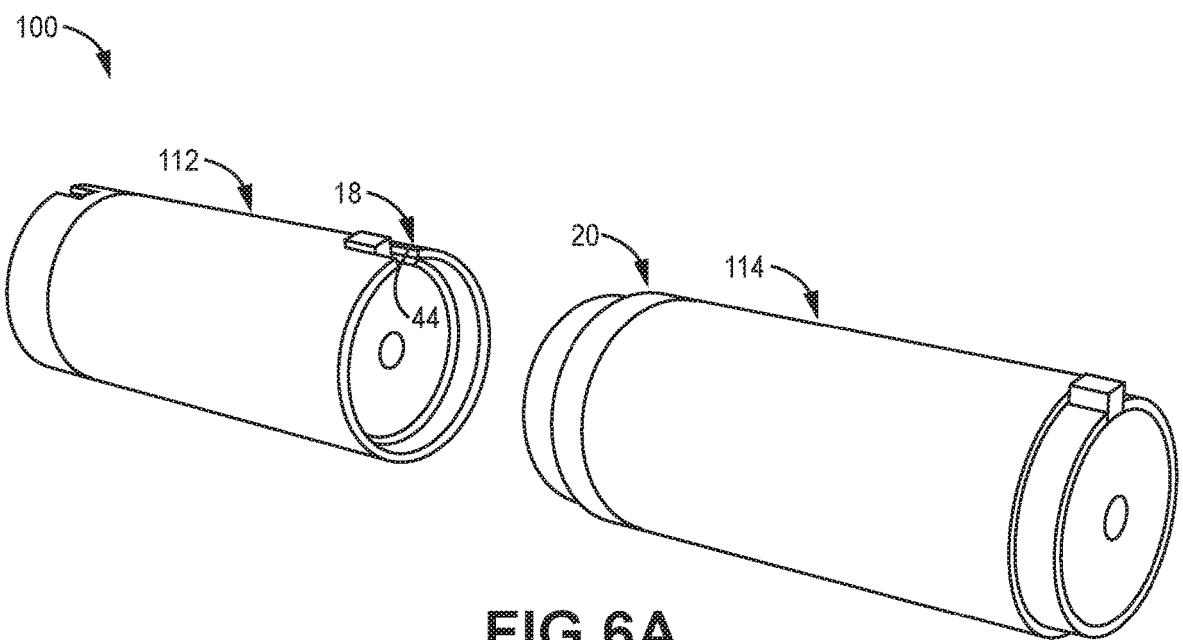
FIGS. 6A-6B are perspective views of the customizable device of FIG. 3B, wherein the first inhalation device and the second inhalation device are coupled so as to be in an inactive configuration and an active configuration, respectively.
Figure 6B:
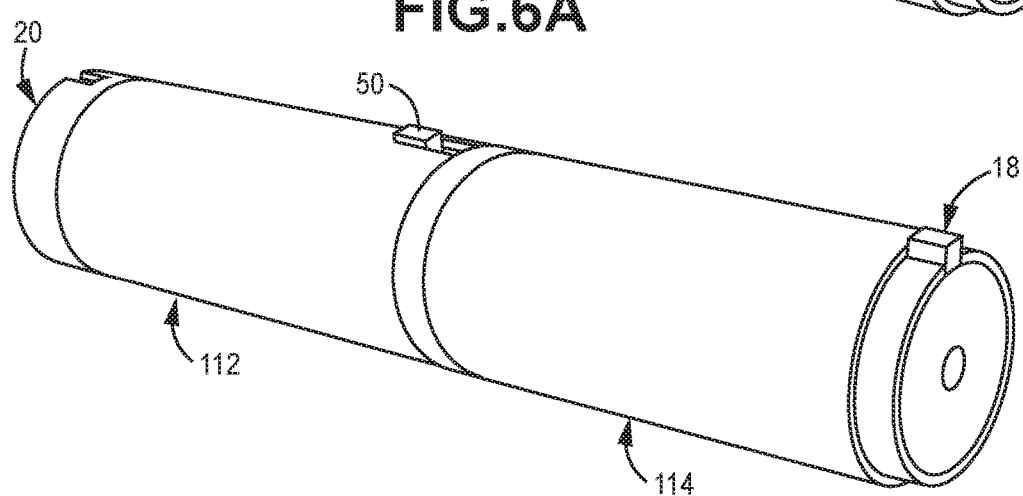
Figure 7A:
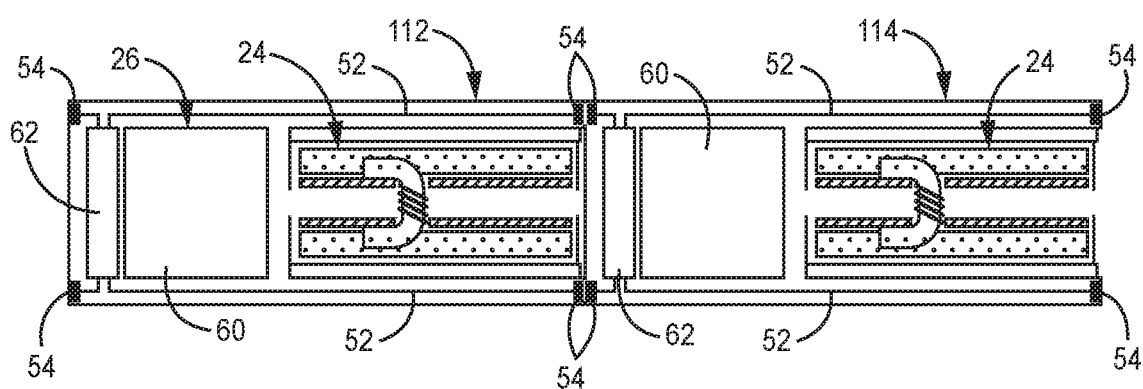
FIG. 7A is a cross-sectional view of a customizable device, wherein the first inhalation device and the second inhalation device are coupled so as to be in an inactive configuration and an active configuration, respectively, according to an example embodiment.
Figure 7B:
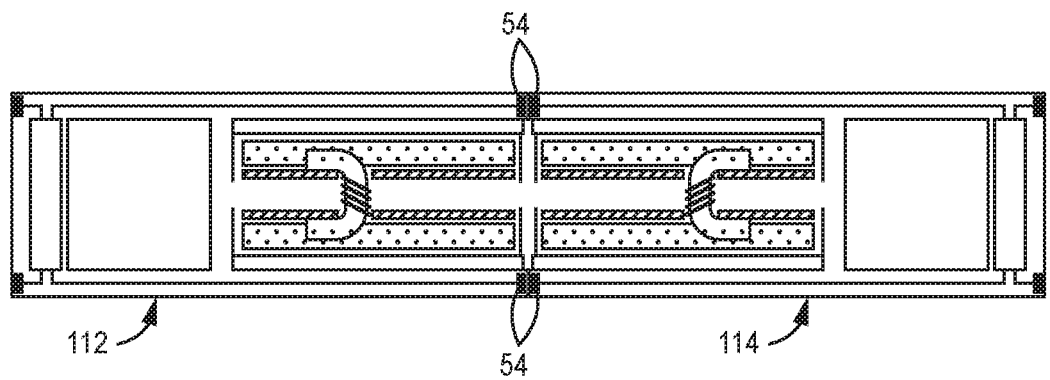
FIG. 7B is a cross-sectional view of the customizable device of FIG. 7A, wherein the first inhalation device and the second inhalation device are coupled so as to both be in an inactive configuration.
Figure 9A:
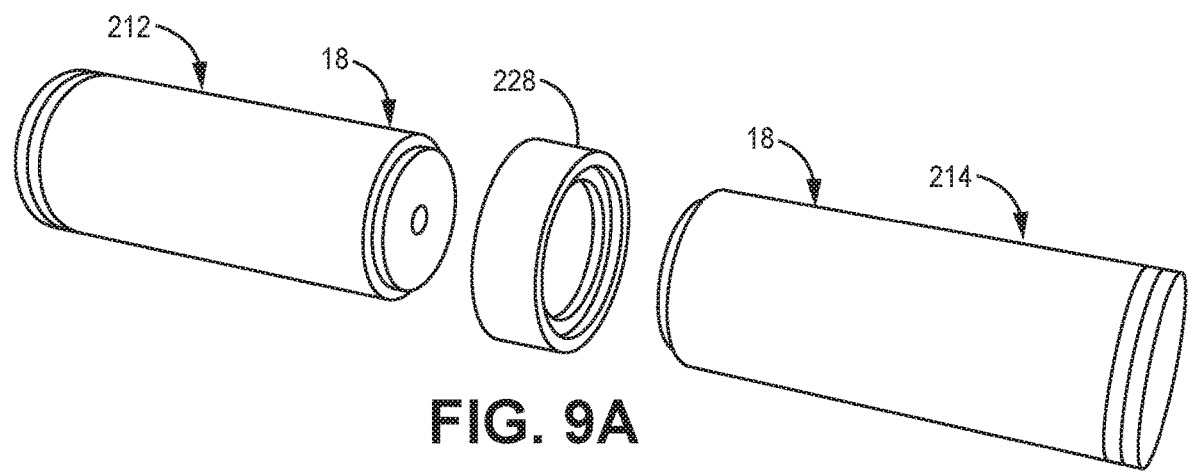
FIGS. 9A-9B are perspective views of a customizable device including the connector hub of FIG. 8C, wherein the first inhalation device and the second inhalation device are coupled so as to both be in an inactive configuration.
Figure 9B:
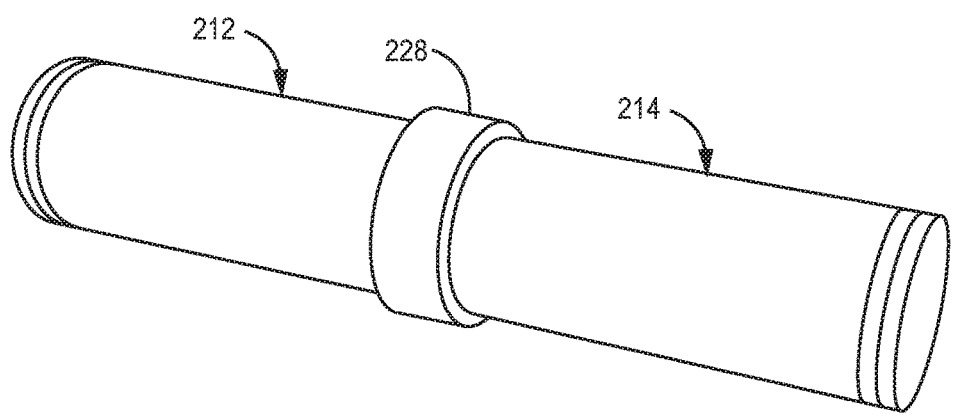

In the second active configuration shown in FIGS. 6A-B, the mouth end portion 18 of the first inhalation device 112 is removably coupled to the upstream end portion 20 of the second inhalation device 114. In this configuration, the second inhalation device 114 is active, whereas the first inhalation device 112 is inactive. Channel 44 is only partially occupied by key 50 of the first consumable device 24.

Each inhalation devices includes a power supply 26 including a power source 60 (e.g., battery) and a controller 62 to regulate power from the power source 60 to other components in the customizable device 100.

Each inhalation device 112, 114 includes electrical or electronic circuitry 52 and electrical contacts 54. The electrical contacts 54 may be exposed axially at the face of the respective inhalation device 112, 114 to electrically couple to electrical contacts on the other inhalation device. Power between the power supplies 26 may be shared via the circuitry 52 and contacts 54. Data may also be shared.

FIGS. 8A-11B show various views of an illustrative customizable device 200 having a first inhalation device 212 and a second inhalation device 214 coupled by a connector hub 228. Many of the parts and components depicted in FIGS. 8A-11B are the same or similar to those depicted in, and described with regard to, FIGS. 1-7B. Reference is made to the discussion above for numbered elements depicted in, but not specifically discussed herein.

The housing 216 of each inhalation device 212, 214 are the same or similar or, at least, define a same outer diameter at each end portion 18, 20. The consumable devices 224 may be partially disposed, or disposed super flush, with the mouth end portions 18, which may facilitate removal of the consumable device from the housing 216. The first and second inhalation devices 212, 214 are couplable via connector hub 228. The connector hub 228 includes a first recess 260 and a second recess 262 opposite the first recess. The recesses 260, 262 may be the same. Each recess 260, 262 has a first inner surface 264 defining a first inner diameter complementary to an outer diameter of the housing 216 at the end portions 18, 20 to removably couple thereto. Each recess includes a shoulder 266 adjacent to the first inner surface 264 defining a second inner surface 268 complementary to an outer diameter of the consumable device 224 at an end portion to removably couple thereto. An intermediate wall 270 may separate the two recesses 260, 262.

Figure 10A:
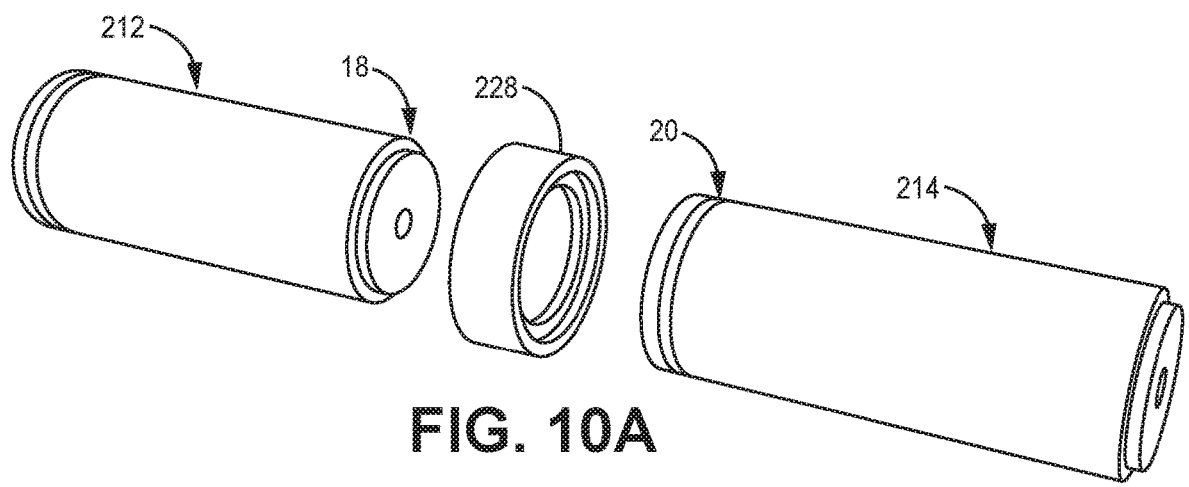
FIGS. 10A-10B are perspective views of a customizable device including the connector hub of FIG. 8C, wherein the first inhalation device and the second inhalation device are coupled so as to be in an inactive configuration and an active configuration, respectively.
Figure 10B:
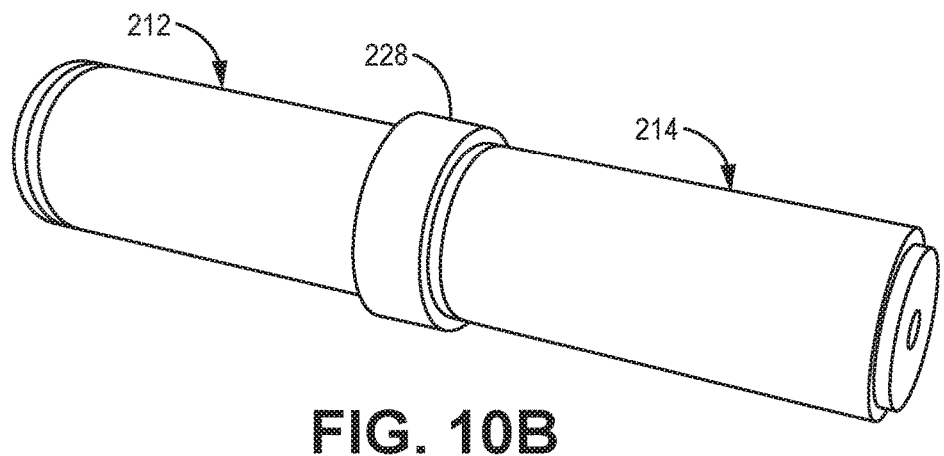
Figure 11A:
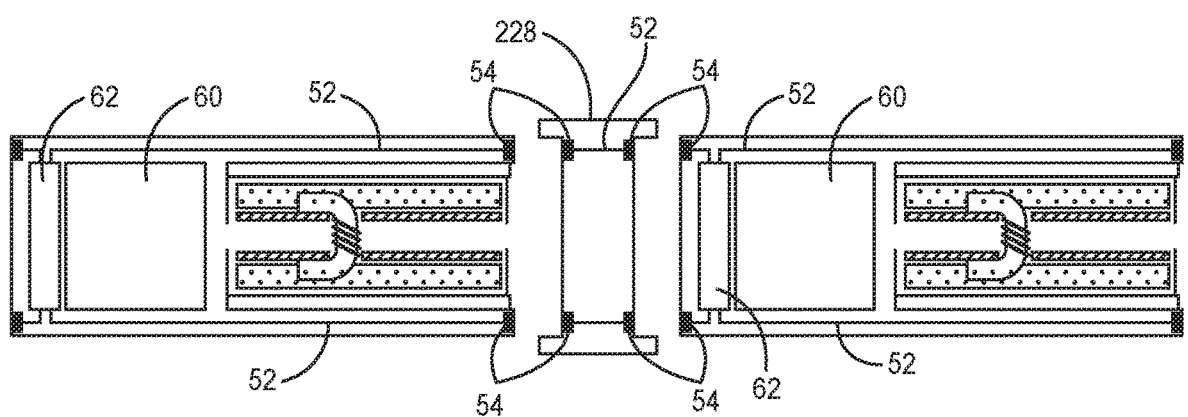
FIGS. 11A-11B are cross-sectional views of a customizable device including a connector hub according to an example embodiment.
Figure 11B:
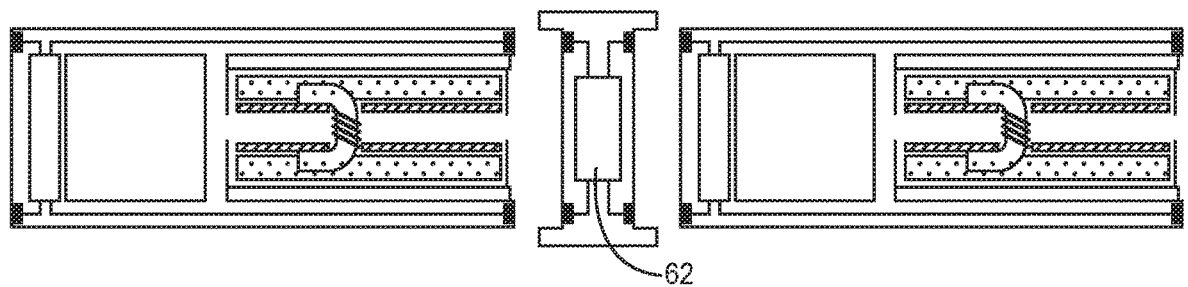

The connector hub 228 enables the customizable device 200 to take on various configurations, such as the storage configuration (FIGS. 9A-B), the first active configuration (not shown), and the second active configuration (FIGS. 10A-10B).

The connector hub 228 includes circuitry 52 and contacts 54 to facilitate electrical coupling between the inhalation devices 212, 214. The connector hub 228 may include a controller 62 to regulate power delivery or other functionality between the inhalation devices 212, 214, as discussed with respect to the inhalation devices 112, 114 shown in FIGS. 3A-7B.

FIGS. 12A-E show cross-sectional views of illustrative inhalation devices 301-305 usable in any of the customizable devices 10, 100, and/or 200 discussed herein. Each of the inhalation devices 301-305 may include a consumable device having a substrate, which may contain nicotine, and a manner of heating the consumable device to generate aerosol.

Inhalation device 301 includes a tobacco consumable device 24a and a heater 64a. The heater 64a is disposed external to the consumable device 24a to heat the tobacco with power from the power source 60 regulated by the controller 62 to heat the substrate.

Inhalation device 302 includes a e-cig consumable device 24b and a mesh heater 64b. The mesh heater 64b is disposed internal to the consumable device 24b and powered by the power source 60 regulated by the controller 62 to heat the substrate.

Inhalation device 303 includes an e-cig consumable device 24c with a susceptor 65c and an induction coil 64c. The induction coil 64c and the susceptor 65c may be considered part of the heater. The induction coil 64c is disposed external to the consumable device 24c and the susceptor 65c is disposed internal to the consumable device. The susceptor 65c is heated using the induction coil 64c powered by the power source 60 regulated by the controller 62 to heat the substrate.

Inhalation device 304 includes a tobacco consumable device 24d with a susceptor 65d and an induction coil 64d. The induction coil 64d and the susceptor 65d may be considered part of the heater. The induction coil 64d is disposed external to the consumable device 24d and the susceptor 65d is disposed internal to the consumable device. The susceptor 65d is heated using the induction coil 64d powered by the power source 60 regulated by the controller 62 to heat the substrate.

Inhalation device 305 includes an e-cig consumable device 24e and a heated coil 64e. The resistive coil heater, or heated coil, 64e is disposed internal to the consumable device 24e and powered by the power source 60 regulated by the controller 62 to heat the substrate.

As depicted, the resistive coil heater 710 is wrapped around at least a portion of a wick 720 configured to pull aerosol-forming fluid 730 from reservoir 740. The resistive coil heater 710 electrically couples to the power source 60 and controller 62 when the consumable device 24 is inserted into the inhalation device 112. An air flow channel 750 is formed in the consumable device 24. At least a portion of the resistive coil heater 710 is in communication with the air flow channel 750. When the resistive coil heater 710 is heated, fluid 730 drawn through the wick 720 in proximity to the resistive coil heater 710 is heated and aerosolized. When a draws occurs on the mouth end of the inhalation device 112, the aerosolized fluid may flow from the inhalation device 112.

Airflow through the inhalation devices 301-305 is shown by the arrows. Similar to the inhalation devices described herein above, the air may enter through an air inlet 32 adjacent to the upstream end portion 20, flow through the consumable device 24a-e, and flow toward the mouth end portion 18 in response to the drawing of air through an inhalation port. The drawn air can be detected by an activator, or puff sensor, of the controller 62 and the consumable device 24a-e can be heated.

Figure 13:
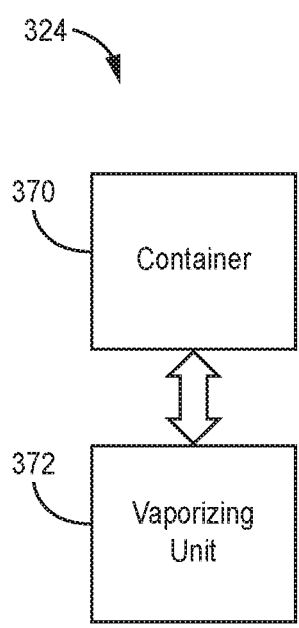
FIG. 13 is a schematic diagram of a multiple-part consumable device according to an example embodiment.

FIG. 13 is a schematic diagram of a multiple-part consumable device 324 usable in any of the customizable devices 10, 100, and/or 200 discussed herein. In an example embodiment, the multiple-part consumable device 324 includes at least two parts, including a container 370 and a vaporizing unit 372. When connected, the vaporizing unit 372 may be powered to vaporize or aerosolize an aerosol-generating substrate in the container 370.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A device comprising:
   a first inhalation device comprising a first housing, a first power supply, and a first consumable device within the first housing, the first power supply configured to provide energy to heat the first consumable device, the first housing having first end portions including a first mouth end portion and a first upstream end portion; and
   a second inhalation device removably couplable to either of the first end portions of the first inhalation device, the second inhalation device comprising a second housing, a second power supply, and a second consumable device within the second housing, the second power supply configured to provide energy to heat the second consumable device, the second housing having second end portions including a second mouth end portion and a second upstream end portion.

2. The device according to claim 1, wherein the first inhalation device is configured to be inactive when the first mouth end portion of the first inhalation device is coupled to the second inhalation device.

3. The device according to claim 1, wherein the first inhalation device is removably couplable to the second upstream end portion of the second inhalation device.

4. The device according to claim 1, wherein each of the first end portions of the first inhalation device defines an axially protruding rim removably couplable to either of the second end portions of the second inhalation device.

5. The device according to claim 1, further comprising:
   a connector hub comprising connector end portions including a first connector end portion and a second connector end portion, the first connector end portion removably couplable to at least the first end portions of the first inhalation device, the second connector end portion removably couplable to at least the second end portions of the second inhalation device.

6. The device according to claim 5, wherein each of the connector end portions of the connector hub is removably couplable to the first end portions of the first inhalation device and the second end portions of the second inhalation device.

7. An assembly comprising:
   a first inhalation including a first power supply, and a first consumable device within the first housing, the first power supply configured to provide energy to heat the first consumable device, the first housing having first end portions including a first mouth end portion and a first upstream end portion, the first housing defining a first cavity extending between the first mouth end portion and the first upstream end portion, the first consumable device defining a first inhalation port and disposed in the first cavity such that the first inhalation port is adjacent to the first mouth end portion; and
   a second inhalation device removably couplable to either of the first end portions of the first inhalation device, the second inhalation device including a second housing, a second power supply, and a second consumable device within the second housing, the second power supply configured to provide energy to heat the second consumable device, the second housing having second end portions including a second mouth end portion and a second upstream end portion, the second housing defining a second cavity extending between the second mouth end portion and the second upstream end portion, the second consumable device defining a second inhalation port and disposed in the second cavity such that the second inhalation port is adjacent to the second mouth end portion.

8. The assembly according to claim 7, wherein at least one of the first consumable device or the second consumable device comprises an aerosol-generating substrate comprising nicotine.

9. The assembly according to claim 7, wherein each of the first mouth end portion of the first inhalation device and the second mouth end portion of the second inhalation device defines a first engagement feature, and each of the first consumable device and the second consumable device comprises a second engagement feature complementary to the first engagement feature to ensure proper alignment.

10. The assembly according to claim 9, wherein the first engagement feature is an axially extending channel, and the second engagement feature is a radially protruding key.

11. The assembly according to claim 7, wherein the first power supply includes a first controller configured to regulate power delivery from the first power supply, and the second power supply includes a second controller configured to regulate power delivery from the second power supply.

12. The assembly according to claim 11, wherein the first controller is electrically coupled to the second controller to regulate power sharing between the first inhalation device and the second inhalation device.

13. A method of using a first inhalation device and a second inhalation device, comprising:

coupling the first inhalation device and the second inhalation device in series to achieve an active configuration or a storage configuration for each of the first inhalation device and the second inhalation device, the first inhalation device including a first housing, a first power supply, and a first consumable device within the first housing, the first power supply configured to provide energy to heat the first consumable device, the first housing having first end portions including a first mouth end portion and a first upstream end portion, the second inhalation device removably couplable to either of the first end portions of the first inhalation device, the second inhalation device including a second housing, a second power supply, and a second consumable device within the second housing, the second power supply configured to provide energy to heat the second consumable device the second housing having second end portions including a second mouth end portion and a second upstream end portion.

14. The method of claim 13, wherein the coupling includes connecting the first upstream end portion of the first inhalation device to the second mouth end portion of the second inhalation device to achieve the active configuration for the first inhalation device and the storage configuration for the second inhalation device.

15. The method of claim 13, wherein the coupling includes connecting the first mouth end portion of the first inhalation device to the second upstream end portion of the second inhalation device to achieve the storage configuration for the first inhalation device and the active configuration for the second inhalation device.

16. The method of claim 13, wherein the coupling includes connecting the first upstream end portion of the first inhalation device to the second upstream end portion of the second inhalation device to achieve the active configuration for both the first inhalation device and the second inhalation device.

17. The method of claim 13, wherein the coupling includes connecting the first mouth end portion of the first inhalation device to the second mouth end portion of the second inhalation device to achieve the storage configuration for both the first inhalation device and the second inhalation device.

* * * * *